(12) United States Patent
Matsumoto et al.

(10) Patent No.: US 6,328,989 B1
(45) Date of Patent: Dec. 11, 2001

(54) USE OF BICOZAMYCIN FOR THE MANUFACTURE OF A MEDICAMENT FOR TREATING INFECTIONS WITH ENTEROHEMORRHAGIC E. COLI

(75) Inventors: Yoshimi Matsumoto, Kyoto; Akiko Ikemoto, Nishinomiya; Chizu Morinaga, Osaka; Shuichi Tawara, Kawanishi; Yoshiko Yokota, Ibaraki, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/555,377

(22) PCT Filed: Nov. 20, 1998

(86) PCT No.: PCT/JP98/05268

§ 371 Date: May 30, 2000

§ 102(e) Date: May 30, 2000

(87) PCT Pub. No.: WO99/27931

PCT Pub. Date: Jun. 10, 1999

(30) Foreign Application Priority Data

Nov. 27, 1997 (AU) .................................................. PP 0598

(51) Int. Cl.$^7$ ........................................................ A61F 13/00
(52) U.S. Cl. ........................ 424/422; 424/400; 424/438; 424/234.1; 424/114
(58) Field of Search ................................ 424/422, 234.1, 424/438, 114, 827

(56) References Cited

U.S. PATENT DOCUMENTS 4,414,204 * 11/1983 Tarcsay et al. ...................... 424/177
5,371,085 * 12/1994 Nakano et al. ...................... 514/249

\* cited by examiner

*Primary Examiner*—Thurman K. Page
*Assistant Examiner*—Liliana Di Nola-Baron
(74) *Attorney, Agent, or Firm*—Oblon, Spivak, McClelland, Maier & Neustadt, P.C.

(57) ABSTRACT

The present invention relates to the use of bicozamycins for the prophylaxis and treatment of infections with a verotoxin-producing *E. coli*, as well as for eradicating verotoxin-producing *E. coli* in livestock.

8 Claims, No Drawings

USE OF BICOZAMYCIN FOR THE MANUFACTURE OF A MEDICAMENT FOR TREATING INFECTIONS WITH ENTEROHEMORRHAGIC E. COLI

FIELD OF THE INVENTION

The present invention relates to new use of bicozamycins. More particularly, it relates to use of bicozamycins for the prophylaxis and treatment of infections with a verotoxin-producing *Escherichia coli*, as well as for eradicating verotoxin-producing *Eschetichia coli* in livestock.

BACKGROUND OF THE INVENTION

There are increasing numbers of reported cases of infections with enterohemorrhagic *Escherichia coli* (EHEC), such as *E. coli* O-157, in recent years. Given that EHEC infection often causes life-threatening diseases such as hemorrhagic colitis, hemolytic uremic syndrome (HUS) and thrombotic thrombocytopenic purpra (TTP), an urgent need exists for establishing a method for the prevention and treatment of EHEC infection. EHEC produces verotoxins which are similar to Shiga toxin produced by *Shigella dysenteriae*, and said verotoxins are considered to be the main pathogen of the above-mentioned serious diseases.

While many antimicrobial agents having a potent antimicrobial effect against a verotoxin-producing *Escherichia coli* (VTEC) are known, almost all of them enhance production of verotoxins or release of them from VTEC. Those antimicrobial agents are not only useless but also harmful, because increased verotoxins often cause severe and fatal symptoms in the patients. A most preferable method for treating VTEC infections has not been established.

Meanwhile, VTEC colonizes in the intestine of livestock such as cow, pig and the like, which most likely carry and transfer VTEC to humans. Therefore, eradication of said VTEC in livestock is extremely important for the prevention of VTEC infection in humans.

SUMMARY OF THE INVENTION

It is therefore an object of the present invention to provide an antimicrobial compound having not only an antimicrobial activity against VTEC, but also a suppressive activity on the production and release of verotoxins, and provide a method for the prophylaxis and treatment of VTEC infections and for eradicating VTEC in livestock, by using said compound. inventors have found the unexpected and surpprising fact that bicozamycin or a derivative thereof (hereinafter also collectively referred to as bicozamycins) have a high suppressive action on the production and release of verotoxins in vitro and in vivo even at the antimicrobially effective concentration against VTEC.

Accordingly, the present invention provides a composition for suppressing the production and/or release of verotoxins, particularly, an agent for the prophylaxis and treatment of VTEC infections, comprising a bicozamicin as an active ingredient. The present invention yet provides an agent for eradicating VTEC in animals.

The present invention also provides a method for suppressing the production and/or release of verotoxins, comprising treating said *E. coli* with an effective amount of a bicozamycin for suppressing production and release of verotoxins. More particularly, the present invention provides a method for the prophylaxis and treatment of VTEC infections, comprising administering a prophylactically and therapeutically effective amount of a bicozamycin. The present invention further provides a method for eradicating VTEC in animals, comprising administering an effective amount of a bicozamycin for eradicating VTEC.

The present invention yet provides use of a bicozamycin for the preparation of a medicament for the suppression of the production and/or release of verotoxins. More particularly, the present invention provides use of a bicozamycin for the preparation of a medicament for the prophylaxis and treatment of VTEC infections. The present invention further provides use of a bicozamycin for the preparation of a medicament for eradicating VTEC in animals.

Furthermore, the present invention provides a commercial package comprising the above-mentioned composition and a written matter associated therewith, the written matter stating that said composition can or should be used for suppressing the production and/or release of verotoxins from VTEC, preventing and treating VTEC infections or eradicating VTEC in animals.

DETAILED DESCRIPTION OF THE INVENTION

Bicozamycin is a known antibiotic produced by *Streptomyces sapporoensis* (ATCC No. 21532) isolated from a soil sample and has been conventionally used for a feed additive and the treatment of bacterial diarrhea in an animal. Bicozamycin can be obtained by, for example, culturing the above-mentioned microorganism, followed by isolation and purification from the culture filtrate using a conventional method known in the art (THE MERCK INDEX, TWELFTH EDITION, 1249 (1996)). In the present invention, bicozamycins may include bicozamycin and a derivative thereof. The derivative is subject to no particular limitation as long as it shows suppression of the production and release of verotoxins, as well as antimicrobial activity against VTEC. Examples thereof include esters (e.g., benzoate, palmitate, etc.) and the like, inclusive of prodrug compounds which show the above-mentioned activities after being metabolized in the body of animals.

Inasmuch as bicozamycins have a suppressive activity on the production and/or release of verotoxins, besides an antimicrobial activity against VTEC, they are useful for the prophylaxis and treatment of diarrhea caused by VTEC infection in a human, and thus, useful for the prophylaxis of complications caused by verotoxins, including hemorrhagic colitis, HUS and TTP. Bicozamycins are also useful for eradicating said VTEC in livestock (e.g., cow, pig, horse, sheep, goat, chicken, etc.), which livestock being the main VTEC infection source for humans.

According to the present invention, a bicozamycin is used in the form of a pharmaceutical preparation comprising said bicozamycin as an active ingredient, in admixture with a pharmaceutically acceptable carrier or excipient suitable for oral or parenteral (inclusive of intravenous, intraperitoneal, subcutaneous and intramuscular injections) administration.

Formulations suitable for oral administration include, for example, solutions containing an effective amount of the active ingredient dissolved in diluents, such as water, saline or orange juice; capsules, sachets and tablets, each containing a predetermined amount of the active ingredient in solids or granules; suspensions using appropriate liquid; and suitable emulsions. Tablets can contain one or more members from lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmaceutically compatible carriers. Lozenge can contain the active ingredient in a flavor, usually sucrose and acacia or tragacanth. Pastilles can contain the active ingredient in an inert base, such as gelatin, glycerol, sucrose and acacia. Emulsions, gels, and the like can contain, in addition to the active ingredient, such excipients as are known in the pertinent art.

Formulations suitable for parenteral administration include aqueous and non-aqueous, isotonic sterile injection solutions, which can contain antioxidants, buffers and solutes that render the formulation isotonic with the blood of an intended recipient, and aqueous and non-aqueous sterile suspensions that can contain suspending agents, solubilizers, thickeners, stabilizers and preservatives. The formulations can be presented in unit-dose or multi-dose sealed containers, such as ampoules and vials, and can be stored in a freeze-dried (lyophilized) condition which will require only the addition of a sterile liquid excipient, such as water, for injections, immediately prior to use.

While the dosage of bicozamycins may vary depending upon recipient species, age and/or body weight of the recipient, administration route, and the like, when the recipient is a human suffering from diarrhea, the preferable dosage of bicozamycins may be selected from the range of 1–100 mg/kg daily for an adult, which may be administered in a single dose or several doses depending on the symptoms.

The following example further illustrates the present invention but, needless to say, should not be construed as in any way limiting its scope.

EXAMPLE 1

(1) Antimicrobial Activity of Bicozamycin Against *E. coli* O-157:H7

The minimum inhibitory concentrations (MICs) of bicozamycin and amoxicillin against *E. coli* O-157:H7 strains were determined by conventional agar dilution method. One hundred-fold dilutions of overnight cultures were inoculated onto Mueller-Hinton agar (Difco) plates containing serially diluted test compounds. The lowest concentration with no visible growth after incubation at 35° C. for 18 hours in aerobic or anaerobic condition was read as MIC. The results are shown in Table 1.

TABLE 1

Antimicrobial susceptibility of *E. coli* O-157:H7
*E. coli* O-157:H7 (20 strains were tested)

| Agent | MIC distribution (μg/ml) | | | | | | | | MIC50 (μg/ml) | MIC90 (μg/ml) |
| --- | --- | --- | --- | --- | --- | --- | --- | --- | --- | --- |
| | 1.56 | 3.13 | 6.25 | 12.5 | 25 | 50 | 100 | >100 | | |
| aerobic | | | | | | | | | | |
| BCM[1] | | | | | 20 | | | | 25 | 25 |
| AMX[2] | | 17 | 2 | | | | | 1 | 3.13 | 6.25 |
| anaerobic | | | | | | | | | | |
| BCM | | | | 15 | 5 | | | | 12.5 | 25 |
| AMX | 14 | 5 | | | | | | 1 | 1.56 | 3.13 |

[1]BCM: Bicozamycin
[2]AMX: Amoxicillin (2) Effect of Bicozamycin on the Production of Verotoxins (VT1 and VT2) and release thereof from *E. coli* O-157:H7

The overnight culture of *E. coli* O-157:H7 strain was centrifuged and the supernatant was removed. The resulting pellet was rinsed once with CAYE (casamino acid yeast extract) broth, resuspended to 107–108 cfu/ml in the CAYE broth, and preincubated for 1 hour in aerobic condition. After treatment with bicozamycin (10, 25 or 100 μg/ml) or amoxicillin (10 μg/ml) at 35° C. for 3 hours, each culture was centrifuged and the supernatant was used as released toxin solution. The resulting pellet was resuspended in the same volume of saline containing 5,000 units of polymixin B and incubated at 35° C. for 30 minutes. After centrifugation at 12,000 rpm for 5 minutes, the supernatant was recovered and used as intracellular toxin solution. The amounts of VT1 and VT2 in both sample solutions were estimated using reversed passive latex agglutination method with VTEC-RPLA detection kit (Seiken). The results are shown in Table 2.

TABLE 2

Effect of bicozamycin on the production of verotoxins and release thereof from *E. coli* O-157:H7

| Agent | Conc. (μg/ml) | VT1 | | VT2 | |
| --- | --- | --- | --- | --- | --- |
| | | released[1] | intracellular[1] | released | intracellular |
| Cont.(0h) | | <2 | 2 | <2 | <2 |
| Cont. | 0 | 2(2)[2] | 64(32) | 8(8) | 16(16) |
| AMX | 10 | ≧256 (≧256) | 64(32) | 8(8) | 4(4) |

TABLE 2-continued

Effect of bicozamycin on the production of verotoxins and release thereof from *E. coli* O-157:H7

| Agent | Conc. (μg/ml) | VT1 released[1] | VT1 intracellular[1] | VT2 released | VT2 intracellular |
|---|---|---|---|---|---|
| BCM | 10 | 8(8) | 32(16) | 2(2) | 4(4) |
| BCM | 25 | 8(8) | 2(1) | <2(1) | <2(1) |
| BCM | 100 | 8(8) | 2(1) | <2(1) | <2(1) |

[1]The amount of toxin was expressed as the maximum dilution times to detect agglutination after treatment with BCM or AMX for 3h.
[2]The values in parentheses show the ratio of the amount of toxin after treatment with BCM or AMX for 3h to the amount of toxin of the control at 0h.

In *E. coli* treated with amoxicillin in a concentration greater than that of MIC, both production and release of verotoxins increased much more than those with an untreated *E. coli*. When *E. coli* treated with bicozamycin in a concentration greater than MIC was used, increases in production and release of verotoxins were dramatically suppressed.

EXAMPLE 2

Therapeutic Effect of Bicozamycin on Mice Infected with *E. coli* O-157

Starting from 4 days prior to the inoculation of *E. coli*, DBA/2 mice (male, 4week-old) were supplied with water containing streptomycin (SM; 5 g/L) for 3 days. Then, said mice were fasted and deprived of water for 1 day. Pre-cultured *E. coli* FP1962 was inoculated into tripticase soy broth containing 5 g/L of SM and incubated with shaking at 35° C. for 4 to 5 hours, and cells were harvested. The cells were suspended in 20% sucrose solution to a turbidity of 2.0 ($4.4 \times 10^9$ cfu/ml) and the cell suspension (0.5 ml/mouse) was orally inoculated to said mice. The mice were divided into 4 groups (Group BCM, Group FOM, Group CAM and Group NFLX; 6 mice in each group). Bicozamycin (32 mg/kg/dose), fosfomycin (32 mg/kg/dose), clathromycin (32 mg/kg/dose) and norfloxacin (10 mg/kg/dose) were respectively administered orally to each group twice a day for 4 days (total 8 times). Six days later, viable cells in the cecum of each mouse were counted after incubation at 35° C. for 18 hours on MacConkey-sorbitol agar (NISSUI) containing 0.05 μg/ml cefixime and 2.5 μg/ml potassium tellurite. The cecum of each mouse was homogenized and centrifuged at 12,000 rpm for 5 minutes. VT1 and VT2 in the supernatant were quantitatively determined using VTEC-RPLA (Seiken) in the same manner as in Example 1 (2). The results are shown in Table 3.

TABLE 3

Effects of various antibiotics on mice infected with *E. coli* O-157

| Group | Individual No. | Number of cells in cecum (cfu/site) | Amounts of VTs in cecum (titer) VT1 | VT2 |
|---|---|---|---|---|
| BCM | 1 | $4.5 \times 10^3$ | <2 | <2 |
| | 2 | $1.0 \times 10^2$ | <2 | <2 |
| | 3 | $1.0 \times 10^2$ | <2 | <2 |
| | 4 | $8.5 \times 10^3$ | <2 | <2 |
| | 5 | $3.5 \times 10^3$ | <2 | <2 |
| | 6 | $1.0 \times 10^5$ | <2 | 2 |
| | mean | $2.2 \times 10^3$ | | |
| FOM | 1 | $7.1 \times 10^5$ | <2 | <2 |
| | 2 | $3.0 \times 10^4$ | <2 | <2 |
| | 3 | $1.2 \times 10^8$ | <2 | 32 |
| | 4 | $4.6 \times 10^7$ | <2 | <2 |
| | 5 | $9.8 \times 10^6$ | <2 | 4 |
| | 6 | $4.9 \times 10^7$ | <2 | 16 |
| | mean | $6.2 \times 10^6$ | | |
| CAM | 1 | $2.4 \times 10^7$ | 2 | 2 |
| | 2 | $7.9 \times 10^7$ | 2 | 4 |
| | 3 | $1.0 \times 10^8$ | 2 | <2 |
| | 4 | $1.3 \times 10^8$ | 2 | 8 |
| | 5 | $7.0 \times 10^6$ | 2 | 2 |
| | 6 | $4.1 \times 10^8$ | 4 | 8 |
| | mean | $6.5 \times 10^7$ | | |
| NFLX | 1 | $6.9 \times 10^5$ | 2 | 16 |
| | 2 | died | | |
| | 3 | died | | |
| | 4 | died | | |
| | 5 | died | | |
| | 6 | died | | |
| | mean | $6.9 \times 10^5$ | | |
| Control | 1 | $2.4 \times 10^8$ | <2 | 8 |
| | 2 | $5.0 \times 10^6$ | <2 | <2 |
| | 3 | $2.0 \times 10^8$ | <2 | 4 |
| | 4 | $2.7 \times 10^8$ | <2 | 4 |
| | 5 | $2.4 \times 10^6$ | <2 | <2 |
| | 6 | $9.8 \times 10^6$ | <2 | <2 |
| | mean | $3.4 \times 10^7$ | | |

Bicozamycin not only showed an antimicrobial activity against VTEC but suppressed the production and release of verotoxins from said *E. coli*. In contrast, other three antiobiotics were ineffective in suppressing the production of verotoxins, and even enhanced the production thereof. Five of 6 tested mice administered with NFLX died due to increased verotoxins, in spite of the fact that NFLX has a strong antibacterial activity against *E. coli*.

This application is based on application No. PP0598/97 filed in Australia, the content of which is incorporated hereinto by reference. All of the references cited herein are hereby incorporated in their entireties by reference.

What is claimed is:

1. A method for suppressing the production of or the release of a verotoxin from a verotoxin-producing *E. coli*, comprising:

contacting said verotoxin-producing *E. coli* with an effective amount of bicozamycin or a derivative thereof.

2. The method of claim 1, wherein said *E. coli* is enterohemorrhagic.

3. A method for treating an animal infected with or carrying a verotoxin-producing *E. coli*, comprising:

administering an effective amount of bicozamycin or a derivative thereof to an animal in need thereof.

4. The method of claim 3, wherein said animal is a livestock animal.

5. A method for eradicating a verotoxin-producing *E. coli* from an animal comprising:

administering an effective amount of bicozamycin or a derivative thereof to an animal carrying verotoxin-producing *E. coli*.

6. The method of claim 5, wherein said animal is a livestock animal.

7. A commercial package comprising:

bicozamycin or a derivative thereof, and written instructions stating that bicozamycin or a derivative thereof can or should be used to suppress or eradicate verotoxin-producing *E. coli* in an animal.

8. The commercial package of claim 7, wherein said animal is a livestock animal.

* * * * *